United States Patent [19]  
Autant et al.

[11] Patent Number: 4,832,967
[45] Date of Patent: May 23, 1989

[54] COMPOSITION FOR FEEDING RUMINANTS CONTAINING A BIOLOGICALLY ACTIVE SUBSTANCE AND ITS PREPARATION

[75] Inventors: Pierre Autant, Commentry; Paul Bourrain, Dardilly; Andre Cartillier, Commentry, all of France

[73] Assignee: Rhone-Poulenc Sante, Courbevoie, France

[21] Appl. No.: 120,666

[22] Filed: Nov. 16, 1987

[30] Foreign Application Priority Data

Nov. 17, 1986 [FR] France ............... 86 15930

[51] Int. Cl.$^4$ .............................................. A23K 1/00
[52] U.S. Cl. ......................................... 426/96; 426/98; 426/302; 426/303; 426/310; 426/807
[58] Field of Search ............. 426/2, 96, 98, 302, 426/303, 310, 807; 424/438, 482, 489

[56] References Cited

U.S. PATENT DOCUMENTS

| | | | |
|---|---|---|---|
| 3,541,204 | 11/1970 | Sibbald et al. | 424/438 |
| 3,615,647 | 10/1971 | Kassens | 426/303 |
| 4,181,710 | 1/1980 | Dannelly et al. | 424/482 |
| 4,194,013 | 3/1980 | Rehacek | 426/96 |
| 4,196,187 | 4/1980 | Dannelly et al. | 424/489 |
| 4,595,584 | 6/1986 | Wu et al. | 424/438 |
| 4,687,676 | 8/1987 | Wu et al. | 424/438 |
| 4,713,245 | 12/1987 | Ando et al. | 426/2 |

FOREIGN PATENT DOCUMENTS

| | | |
|---|---|---|
| 5146085 | 12/1985 | Australia . |
| 0188953 | 7/1986 | European Pat. Off. . |
| 2401620 | 3/1979 | France . |
| 2401619 | 3/1979 | France . |
| 2565101 | 12/1985 | France . |
| 2005537 | 4/1979 | United Kingdom . |
| 2006009 | 5/1979 | United Kingdom . |
| 2160096 | 12/1985 | United Kingdom . |
| 8404657 | 12/1984 | World Int. Prop. O. . |

*Primary Examiner*—R. B. Penland
*Attorney, Agent, or Firm*—Stevens, Davis, Miller & Mosher

[57] ABSTRACT

Composition for feeding ruminants, containing a water-soluble biologically active substance which is stable in a medium whose pH is greater than or equal to 5 and which permits the release of the active substance in a medium whose pH is less than 3.5, comprising:

a core containing the active substance, which has optionally undergone a surface treatment, a first coating layer consisting of a film-forming substance sensitive to pH variations, optionally in combination with an inorganic filler, and a second coating layer consisting of a hydrophobic substance, optionally in combination with an inorganic filler.

19 Claims, No Drawings

COMPOSITION FOR FEEDING RUMINANTS CONTAINING A BIOLOGICALLY ACTIVE SUBSTANCE AND ITS PREPARATION

The present invention relates to compositions for feeding ruminants containing a water-soluble biologically active substance, which are stable in a medium whose pH is equal to or greater than 5.5 and which permit the release of the active substance in a medium whose pH is equal to or less than 3.5.

When certain biologically active substances (e.g. drugs or enriched feeds) are administered to ruminants, an enzymatic destruction of these substances, favoured by the residence time (which may be from a few hours to several days) and by the pH (between 5 and 6), occurs during the passage through the rumen.

It is hence important to protect such biologically active substances by coatings which are stable in the rumen of the ruminants, which resist degradation by microorganssms, and which permit the release of the biologically active substances in a part of the digestive system, more especially in the abomasum, in which the pH is less than or equal to 3.5. Whereas the period of protection in the rumen has to be relatively long (several hours to a few days), the release of the active substance in the abomasum must be accomplished in a relatively short time (from a few minutes to 1 or 2 hours).

Many coating compositions have been described, e.g. in French Pat. Nos. FR 78/23,966 (2,401,620), FR 78/23,968 (2,401,621) or FR 81/18,954 (2,514,261). However, while these compositions give satisfactory results when they are used for coating substances of relatively low solubility in water (e.g. methionine, whose solubility is in the region of 40 g/liter), they are not completely suitable for coating substances whose solubility in water is higher (e.g. lysine hydrochloride, whose solubility is in the region of 400 g/liter).

The present invention provides compositions for feeding ruminants containing a water-soluble, biologically active substance, which are stable in a medium whose pH is equal to or greater than 5.5 and which permits the release of the active substance in a medium whose pH is equal to or less than 3.5, which comprises:

(1) a core which has optionally undergone a surface treatment, consisting of the water-soluble biologically active substance or of a composition containing the said substance;

(2) a first coating layer consisting of a substance or composition that is sensitive to pH variations, and optionally an inorganic filler; and (3) a second coating layer consisting of a hydrophobic substance or composition, and optionally an inorganic filler, provided that when the core has not undergone a surface treatment; the precoating layer and optionally the outer coating layer contain an inorganic filler.

The surface treatment of the granules to be coated consists in praying the surface of the granules with a solution of a binder that is hydrophobic in nature, optionally containing a dispersion of an inorganic filler that is somewhat hydrophilic in nature.

The binder is preferably a hydrophobic polymer such as zein, ethylcellulose or cellulose acetobutyrate. The binder can also consist of a polymer sensitive to pH variations, such as a copolymer of styrene with vinylpyridines, optionally in combination with a hydrophobic substance such as a fatty acid, a fatty ester or a fatty alcohol.

The inorganic fillers are chosen, more especially, from pyrogenic or precipitated silicas, e.g. Aerosil 300 and levilite, calcium carbonate or kaolin.

Since the stability at pH 6 of the surface-treated granule increases with the content of binder, there is theoretically no upper limit to the content of binder. However, in order to obtain a finished granule whose content of biologically active substance is sufficient, it is especially advantageous to limit the content of binder to a value in the region of 10% of the weight of the granule to be coated.

In general, the hydrophilic inorganic filler represents up to 10% by weight of the granule to be coated, a greater content not leading to a significant increase in the stability at pH 6.

The precoating layer generally consists of a film-forming basic polymer sensitive to pH variations, optionally in combination with a non-water-soluble polymer and/or a hydrophobic substance, in which polymer a hydrophobic inorganic lamellar or pulverulent filler is optionally dispersed.

Among basic aminated polymers, there may be mentioned polymers containing at least one basic amino group and whose content of basic nitrogen is between 2 and 14%, such as amino derivatives of cellulose, polymers and copolymers of amino derivatives of acrylic, methacrylic and crotonic acids, and polymers or copolymers of styrene or acrylonitrile with isomers or derivatives of vinylpyridine such as 2-vinylpyridine, 4vinylpyridine or 2-methyl-5-vinylpyridine. Of very special value are the copolymers of styrene with isomers or derivatives of vinylpyridine, and more especially the copolymers of styrene with 2-vinylpyridine.

The non-water-soluble polymer is generally chosen from cellulose derivatives such as ethylcellulose, cellulose acetobutyrate and cellulose propionate, or zein.

The hydrophobic substances are generally chosen from fatty acids, fatty esters, fatty alcohols and mixtures thereof. Of very special value are the hydrophobic substances whose melting point is above 60° C., and more especially stearic acid whose purity is greater than 90% and behenic acid.

The inorganic fillers which are especially suitable are lamellar fillers such as aluminum flakes and talc or silicas. Hydrophobic treated silicas are more especially effective.

In general, in the precoating composition, the basic polymer, optionally in combination with the non-water-soluble polymer represents 0.5 to 10% and preferably 0.8 to 6% by weight of the core, and the inorganic filler represents 5 to 15% and preferably 8 to 12% by weight of the core.

In general, the precoating layer has a thickness of between 5 and 10 microns.

When the core has undergone a surface treatment, it is especially advantageous to use a precoating composition consisting of a basic copolymer in combination with a hydrophobic substance whose melting point is above 60° C., in order to limit the amount of basic aminated polymer. In general, the basic copolymer/hydrophobic substance ratio is between 5:95 and 50:50, and more especially between 10:90 and 20:80.

The outer coating layer generally consists of a mixture of hydrophobic substances. The hydrophobic substances are chosen in such a way that the outer coating layer possesses a texture which permits the diffusion or penetration of the external liquid medium. In addition to a low permeability to water, the hydrophobic substances must have suitable mechanical properties, such as high tensile strength and elongation resistance, and film-forming nature.

Among the hydrophobic substances, there may be mentioned fats, paraffin waxes, natural waxes (carnauba wax, beeswax), synthetic waxes (polyethylene wax), polymers such as polyethylene, polypropylene, polybutenes, polyisobutenes, polypentenes, polystyrene, polyvinyl chloride or fluoride, polyvinylidene chloride or fluoride, polyphenylenes, polyphenylene oxides, polybutadiene, polyisoprene or polychloroprene, polyvinyl acetate, non-water-soluble cellulose derivatives and latexes: the hydrophobic substances may be used alone, but preferably as a mixture so as to obtain an outer layer having the desired mechanical properties.

The thickness of the outer coating layer is linked to the viscosity of the hydrophobic composition in the molten state.

In order to obtain a thin outer coating, it is especially advantageous that the viscosity in the molten state should be between 2 and 10 poises.

When the viscosity is too low, the coating is not satisfactory. When the viscosity is too high, the outer coating layer is too thick and agglomeration phenomena occur.

It is especially advantageous to use an outer coating composition consisting of a film-forming hydrophobic polymer (such as polyethylene), a diluent which decreases the viscosity of the molten phase (such as a paraffin wax melting in the region of 60° C.) and an agent providing for the mechanical behaviour which possesses great fluidity in the molten state and great hardness in the solid state (such as Polywax 500 or polyethylene wax), thereby imparting good mechanical strength and avoiding sticking at the temperature of use.

In the compositions according to the invention, the outer coating layer, whose average thickness can vary from 5 to 200 microns according to the size of the granule to be coated, represents from 1 to 50% of the total weight of the composition.

In order to improve the properties of the compositions according to the invention, it can be advantageous to add a pulverulent inorganic filler, chosen from pyrogenic or precipitated silicas, to the hydrophobic outer coating composition. The content of inorganic filler generally represents from 0.1 to 30% and preferably from 1 to 15% by weight of the outer coating composition.

According to the present invention, the compositions can contain additives whose role is to facilitate the implementation of the techniques for preparing these compositions or to improve the physicochemical characteristics. It can be advantageous to add plasticizers (triacetin, propylene glycol), lubricating agents (magnesium stearate), binding agents (polyvinylpyrrolidone, polyvinyl alcohol, gelatin), antistatic agents (triglycerides containing polyoxymethylenated chains), anticaking agents, fungicidal agents, emulsifying agents, agents for improving compatibility, sugars, starches or proteins. These additive derivatives generally represent only a few percent by weight of the coating.

The active substances participating in the compositions according to the invention are various therapeutic or nutrient substances designed to be administered orally to ruminants, and more especially those substances whose solubility in water is high and generally greater than 1,00 g/liter. Among these active substances, lysine hydrochloride may be mentioned more especially.

The new compositions according to the invention are preferably granules, generally spherical or cylindrical, whose average diameter is between 0.05 and 5 mm.

The new compositions according to the invention may be prepared by application of the known techniques of granulation and coating.

The surface treatment of the core is generally carried out by spray-coating with a dispersion of the inorganic filler in an organic solution of the binder.

The precoating of the surface-treated granules may be performed according to the usual coating techniques, such as encapsulation in a fluidized bed, immersion or coacervation.

To produce the outer coating on the precoated active substance, various techniques may be used.

It is possible to perform the outer coating operation in a fluidized bed, by immersion, by adsorption in liquid medium or by coacervation.

It is also possible to perform the operation of coating with the molten or dissolved hydrophobic substance by projecting a suspension of the precoated active substance, in the molten substance or the substance dissolved in a suitable organic solvent in which the precoated active substance is insoluble, onto a flat or concave disc, optionally incorporating grooves, rotating at a specified speed and heated with hot air, generally to a temperature 20° C. above the solidification temperature of the hydrophobic composition. In general, the precoated active substance is dispersed in twice its weight of hydrophobic composition.

The excess hydrophobic composition forms small particles which fall in the vicinity of the disc whereas the particles of coated active substance are ejected further. As a result, the separation of the particles of coated active substance and the particles of hydrophobic composition is accomplished systematically in the course of carrying out the process. Furthermore, the excess hydropobic composition can be recycled.

The examples which follow show how the invention may be put into practice.

The surface treatment is performed by spray-coating with a dispersion of the inorganic filler in a solution of the binder in an organic solvent [methylene chloride/methanol (50:50 by volume)].

The precoating is performed by treating the granules, optionally pretreated in a fluidized bed, with a solution in an organic solvent (tetrahydrofuran, methylene chloride) of the precoating composition which is sensitive to pH variations, optionally containing a dispersed inorganic filler.

The outer coating operation is performed by dispersing precoated granules (50 g) in molten hydrophobic composition (100 g) optionally containing a dispersed inorganic filler, and then by running the dispersion onto the center of a horizontal disc rotating at a speed in the region of 1,500 rpm and whose temperature is maintained above the melting point of the hydrophobic composition. The granules are ejected from the disc, the film solidifying through spontaneous cooling during the trajectory of fall.

The release of the active substance contained in the granules obtained is examined, under specified conditions, by agitating a known quantity of granules in a buffered medium maintained at constant pH at a temperature of 40° C. The rates of release from a sample subjected to different pH values are compared.

The resistance to the rumen is determined in the following manner:

The test sample (approximately 200 mg) is weighed exactly and introduced into a nylon bag whose mesh aperture is 300×300 microns. The bags are closed by heat sealing and incubated in the rumen of fistulated ewes. After 48 hours, the bags are recovered and rinsed and the remaining active principle is assayed.

EXAMPLE 1

(comparative example)

Methionine in the form of granules whose average diameter is between 0.50 and 0.63 mm is precoated with a 2-vinylpyridine/styrene copolymer so that the thickness of the precoating layer is in the region of 8 microns.

The granules thereby obtained are coated with a hydrophobic composition consisting of low molecular weight polyethylene (20), polyethylene wax (50) and paraffin wax melting at 60° C. (30).

Granules are thereby obtained whose methionine titre is in the region of 60%.

The results of the release experiments are given in Table 1.

EXAMPLE 2

(comparative example)

The procedure is as in Example 1, but with methionine replaced by lysine hydrochloride.

The results of the release experiments are given in Table 1.

TABLE 1

| | | % released at 40° C.* | | | |
|---|---|---|---|---|---|
| | | pH 6 | | pH 2 | |
| Example | Titre | after 5 hours | after 24 hours | after 2 hours | % resistance to the rumen |
| 1 | 60 | 2 | 2 | 96 | 90 ± 9 |
| 2 | 61 | 100 | | 100 | 0 |

*in the presence of 0.5% of Tween 80

These Examples show that it is much more difficult to protect the very soluble lysine hydrochloride than the relatively insoluble methionine.

EXAMPLES 3 to 14

Lysine hydrochloride containing 15% of Avicel (microcrystalline cellulose) is used in the form of granules whose average diameter is between 0.8 and 1 mm.

The granules are pretreated (except in Examples 3 and 4) with zein (10% by weight of the granules) containing inorganic fillers.

The precoating is carried out with a 2-vinylpyridine/styrene (70:30) copolymer in such a way that the precoating represents 4% of the weight of the core.

The outer coating operation is carried out with a composition consisting of low molecular mass polyethylene (20), polyethylene wax (50) and paraffin wax (30) (composition P), optionally containing Aerosil 300 (4) (composition Q).

The results of the experiments assessing release and assessing resistance to the rumen are given in Table 2.

TABLE 2

| | | | | % release at 40° C.* | | | |
|---|---|---|---|---|---|---|---|
| | | | Lysine.HCl | at pH 6 | | at pH 2 | % resistance |
| Example | Surface treatment | Outer coating | titre % | after 5 hours | after 24 hours | after 2 hours | to the rumen (48 h) |
| 3 (comparative) | — | P | 54 | 97 | 100 | 100 | 24 ± 2 |
| 4 (comparative) | — | Q | 57 | 51 | 76 | 93 | 29 ± 2 |
| 5 | zein (10%) | P | 50 | 34 | 78 | 100 | |
| 6 | zein (10%) | Q | 50 | 14 | 58 | 100 | 46 ± 3 |
| 7 | zein (10%) CaCO3 (10%) | P | 52 | 17 | 71 | 100 | 73 ± 3 |
| 8 | zein (10%) CaCO3 (5%) | P | 55 | 33 | 68 | 93 | 49 ± 4 |
| 9 | zein (10%) CaCO3 (5%) | Q | 48 | 5 | 9 | 82 | 84 ± 2 |
| 10 | zein (10%) kaolin (10%) | P | 49 | | 39 | 97 | 60 ± 2 |
| 11 | zein (10%) kaolin (10%) | Q | 47 | | 14 | 100 | 91 ± 3 |
| 12 | zein (10%) Aerosil 300 (10%) | P | 50 | | 15 | 95 | 80 ± 4 |
| 13 | zein (10%) Aerosil 300 (10%) | Q | 45 | | 7 | 85 | 96 ± 4 |
| 14 | zein (10%) levilite (10%) | P | 50 | 8 | 20 | 100 | 81.5 ± 7.7 |

*in the presence of 0.5% of Tween 80

EXAMPLES 15 to 16

The procedure is as in Examples 3 to 14, using lysine hydrochloride containing 15% of Avicel (microcrystalline cellulose) in the form of granules whose average diameter is between 0.8 and 1 mm.

The surface treatment is performed with a composition containing ethylcellulose (10% by weight of the core) and Aerosil 300 (10% by weight of the core).

The precoating is performed with a composition that is sensitive to pH variations, consisting of 2-vinylpyridine/styrene (70:30) copolymer and stearic acid (20:80 by weight).

The outer coating operation is performed either with the composition P or with the composition Q which are described above.

The results of the experiments assessing release and assessing resistance to the rumen are given in Table 3.

TABLE 3

| Example | Outer coating | Lysine.HCl titre % | % release at 40° C. at pH 6* after 5 h | after 24 h | % resistance to the rumen (48 h) |
|---|---|---|---|---|---|
| 15 | P | 49.8 | 12 | 21 | 89.6 ± 2.8 |
| 16 | Q | 50.2 | 12 | 24 | 78.0 ± 0.5 |

*in the presence of 0.5% of Tween 80.

EXAMPLES 17 to 27

Lysine hydrochloride containing 15% of Avicel (microcrystalline cellulose) is used in the form of granules whose average diameter is between 0.8 and 1 mm and which are not pretreated.

The precoating is performed with a 2-vinyl-pyridine/styrene (2VP/S) (70:30) copolymer containing a dispersed inorganic filler.

The outer coating operation is performed either with the composition P or with the composition Q which are described above.

The results of the experiments assessing release and assessing resistance to the rumen are collated in Table 4.

TABLE 4

| Example | Precoating | Outer coating | Lysine.HCL titre % | % release at 20° C. at pH 6 after 8 h | after 24 h | at pH 2 after 2 h | % resistance to the rumen (48 h) |
|---|---|---|---|---|---|---|---|
| 17 | 2VP/S (4%) | P | 59 | | 96 | 98 | 8 ± 1 |
| 18 | 2VP/S (4%) | Q | 57 | | 51 | | 33 ± 2 |
| 19 | 2VP/S (4%) Al flakes (6%) | P | 53 | 10 | 18 | 99 | 77 ± 6 |
| 20 | 2VP/S (4%) Al flakes (6%) | Q | 48 | 15 | 21 | 67 | |
| 21 | 2VP/S (4%) Aerosil 300 (10%) | P | 55 | 12 | 20 | 64 | 80 ± 2 |
| 22 | 2VP/S (4%) Aerosil 300 (10%) | Q | 47 | 7 | 9 | 34 | 80 ± 2 |
| 23 | 2VP/S (4%) Aerosil 300 (5%) | P | 52 | 20 | 25 | 91 | 71 |
| 24 | 2VP/S (4%) Aerosil 300 (5%) | Q | 47 | 27 | 26 | 85 | 71 ± 5 |
| 25 | 2VP/S (4%) Sipernat 17 (10%) | P | 50 | 20 | 29 | 100 | 78.0 ± 2.8 |
| 26 | 2VP/S (4%) Aerosil R 972 (10%) | P | 49 | 19 | 37 | | 60.8 ± 5.7 |
| 27 | 2VP/S (4%) talc (10%) | P | 52 | 18 | 37 | 100 | 61.7 ± 7.2 |

*in the presence of 0.5% of Tween 80.

EXAMPLES 28 to 30

Lysine hydrochloride containing 15% of Avicel (microcrystalline cellulose) is used in the form of granules whose average diameter is between 0.8 and 1 mm.

The granules are surface treated with a composition containing 10% by weight of the core of zein and 10% by weight of the core of kaolin.

The precoating composition consists of 2-vinyl-pyridine/styrene (70:30) copolymer. The precoating represents approximately 4% of the weight of the core (thickness in the region of 7 microns).

The outer coating operation is carried out with low molecular weight polyethylene (20), Polywax 500 (50), paraffin wax (30) and an inorganic filler. The content of inorganic Filler in the outer coating composition ia determined in such a way that the viscosity of the molten mixture is the same in all the experiments.

The results of the experiments assessing release and assessing resistance to the rumen are collated in Table 5.

TABLE 5

| Example | Mineral filler | Content for 100 parts of hydrophobic composition | Lysine.HCl titre % | % release at 40° C. at pH 6 after 5 h | after 24 h | % resistance to the rumen (48 h) |
|---|---|---|---|---|---|---|
| 28 | — | — | 53 | 21 | 78 | 43.0 ± 9.8 |
| 29 | Aerosil 300 | 4 | 49 | 6 | 21 | 87.9 ± 6.1 |
| 30 | Levilite | 12 | 50 | 3 | 10 | 80.3 ± 1.3 |

For the composition of example 30, the percentage of release at pH = 2 is 92 after 2 hours at 40° C.

We claim:

1. A composition for feeding ruminants containing a water-soluble biologically active substance, which is stable in a medium whose pH is equal to or greater than 5.5 and which permits the release of the active substance in a medium whose pH is equal to or less than 3.5, which consists essentially of:
   (1) a core consisting of the water-soluble biologically active substance or of a composition containing the said substance;
   (2) a first coating layer consisting of a substance or composition that is sensitive to pH variations, or consisting of an inorganic filler and a composition or substance that is sensitive to pH variations; and (3) a second coating layer consisting of a hydrophobic substance or composition, or consisting of a hydrophobic substance and an inorganic filler, provided that when the core has not undergone a surface treatment, the first coating layer contains an inorganic filler or the first coating layer and the outer coating layer both contain an inorganic filler.

2. The composition according to claim 1, in which the core has been surface-treated with a composition consisting of a hydrophobic binder, or consisting of a hydrophobic binder containing a hydrophilic inorganic filler.

3. The composition according to claim 2, in which the binder contains, as the inorganic filler pyrogenic or precipitated silica, calcium carbonate or kaolin.

4. The composition according to claim 2, in which the binder is zein, ethylcellulose or cellulose acetobutyrate, or a basic copolymer sensitive to pH variations or the binder is a hydrophobic substance in combination with zein, ethylcellulose or cellulose acetobutyrate or a basic copolymer sensitive to pH variations.

5. The composition according to claim 1, in which the first layer consists of a film-forming basic aminated polymer sensitive to Ph variations or consists of a film-forming basic aminated polymer sensitive to pH variations and at least one substance from the group comprising a non-water-soluble polymer, a hydrophobic substance, a dispersed lamellar inorganic filler and a dispersed silica.

6. The composition according to claim 5, in which the basic aminated polymer is an amino derivative of cellulose, a polymer or copolymer of an amino derivative of acrylic, methacrylic or crotonic acid, or a polymer or copolymer of styrene or acrylonitrile with an isomer or derivative of vinylpyridine.

7. The composition according to claim 6, in which the basic aminated polymer is a copolymer of styrene with 2-vinylpyridine, 4-vinylpyridine or 2-methyl-5-vinylpyridine.

8. The composition according to claim 5, in which the said non-water-soluble polymer is ethylcellulose, cellulose acetobutyrate, cellulose propionate or zein.

9. The composition according to claim 5, in which the hydrophobic substance is a fatty acid, fatty ester, fatty alcohol or a mixture thereof.

10. The composition according to claim 9, in which the hydrophobic substance is stearic acid having a purity greater than 90%.

11. The composition according to claim 5, in which the inorganic filler present in the first and/or second layer is aluminum flakes, talc, or a silica.

12. The composition according to claim 11, in which the silica is a hydrophobic treated silica.

13. The composition according to claim 12, in which the silica is pyrogenic or precipitated silica.

14. The composition according to claim 1, in which the biologically active substance is a water-soluble therapeutic or nutrient substance.

15. The composition according to claim 14, in which the biologically active substance is lysine hydrochloride.

16. The composition according to claim 1, in which the hydrophobic substance of the second layer consists of a fat, paraffin wax, natural or synthetic wax, polyethylene, polypropylene, a polybutene, a polyisobutene, a polypentene, polystyrene, polyvinyl chloride or fluoride, polyvinylidene chloride or fluoride, a polyphenylene, a polyphenylene oxide, polybutadiene, polyisoprene, polychloroprene, polyvinyl acetate, a non-water-soluble cellulose derivative or a latex, or a mixture thereof.

17. The composition according to claim 16, in which the said hydrophobic substance consists of a mixture of low molecular weight polyethylene, a polyethylene wax and a paraffin wax.

18. A process for preparing a composition for feeding ruminants containing a water-soluble biologically active substance, which is stable in a medium whose pH is equal to or greater than 5.5 and which permits the release of the active substance in a medium whose pH is equal to or less than 3.5, which consists essentially of forming a pre-coated granule by coating a core granule containing the biologically active substance, with a first coating layer consisting of a substance or composition that is sensitive to pH variations or consisting of a substance or composition that is sensitive to pH variations and an inorganic filler, by an encapsulation technique in a fluidized bed, by immersion or by coacervation, and then coating the precoated granule thereby obtained with a second coating layer consisting of a hydrophobic substance or composition, or consisting of a hydrophobic substance or composition and an inorganic filler, by encapsulation in a fluidized bed, by immersion, by absorption in liquid medium or by coacervation, provided that when the core has not undergone a surface treatment, either the first coating layer or both the first coating layer and the outer coating layer contains an inorganic filler.

19. The process according to claim 18, wherein the second coating operation is performed by projecting a dispersion of the coated granules in the molten hydrophobic substance or the hydrophobic substance dissolved in a suitable organic solvent onto a horizontal rotating disc.

* * * * *